United States Patent
Jo et al.

(10) Patent No.: US 8,319,125 B2
(45) Date of Patent: Nov. 27, 2012

(54) PEDAL INPUT DEVICE WITH THREE ROTATIONAL DEGREES OF FREEDOM

(75) Inventors: Yung Ho Jo, Gyeonggi-do (KR); Du-Jin Bach, Gyeonggi-do (KR); Hye Won Im, Gyeonggi-do (KR); Young Woo Kim, Gyeonggi-do (KR)

(73) Assignee: National Cancer Center, Gyeonggi-do (KR)

( * ) Notice: Subject to any disclaimer, the term of this patent is extended or adjusted under 35 U.S.C. 154(b) by 524 days.

(21) Appl. No.: 12/504,065

(22) Filed: Jul. 16, 2009

(65) Prior Publication Data

US 2010/0230259 A1    Sep. 16, 2010

(30) Foreign Application Priority Data

Mar. 12, 2009  (KR) .................. 10-2009-0021232

(51) Int. Cl.
*H01H 3/14* (2006.01)
(52) U.S. Cl. ....................................... 200/86.5; 200/6 A
(58) Field of Classification Search .................. 200/86.5, 200/6 A
See application file for complete search history.

(56) References Cited

U.S. PATENT DOCUMENTS

| | | | |
|---|---|---|---|
| 3,980,848 A * | 9/1976 | Schulz et al. | 200/86.5 |
| 5,621,196 A * | 4/1997 | Nishijima et al. | 200/6 A |
| 5,787,760 A | 8/1998 | Thorlakson | |
| 6,132,313 A | 10/2000 | Yamaguchi | |
| 7,214,894 B1 * | 5/2007 | Kakuno et al. | 200/6 A |

FOREIGN PATENT DOCUMENTS

| | | |
|---|---|---|
| JP | 57-189412 A | 11/1982 |
| JP | 60-149034 U | 10/1985 |
| JP | 2-181325 A | 7/1990 |

OTHER PUBLICATIONS

Japanese Office Action issue in related application No. 2009-151692,mail date Sep. 27, 2011, 5 pages.

* cited by examiner

*Primary Examiner* — Renee Luebke
*Assistant Examiner* — Lheiren Mae Caroc
(74) *Attorney, Agent, or Firm* — Bacon & Thomas, PLLC

(57) ABSTRACT

A pedal input device includes a base plate; a rotation center portion provided at the center of the base plate; a contacting plate having a yaw switch contacting portion protruding downwards from lower surface of the contacting plate; a pedal plate carried by the contacting plate and foot-operated so as to cause a drive member to make three-degree-of-freedom movement; a pair of pitch switches installed on the base plate in an opposing relationship with each other; a pair of roll switches installed on the base plate in an perpendicular relationship to the pitch switches so that the roll switches can be alternately contacted to the contacting plate of the pedal plate; and a pair of yaw switches installed on the base plate in an spaced-apart relationship with each other so that the yaw switches can be alternately contacted to the yaw switch contacting portion as the pedal plate rotates.

16 Claims, 3 Drawing Sheets

PEDAL INPUT DEVICE WITH THREE ROTATIONAL DEGREES OF FREEDOM

FIELD OF THE INVENTION

The present invention relates to a pedal input device with three rotational degrees of freedom and, more specifically, to a pedal input device for use in a mechanical, pressure-operated or electric manipulation apparatus operable with a minimized motion of the user's foot. With the pedal input device, a user can easily operate a drive member so as to make three-degree-of-freedom movement including translational movement, namely the combination of roll, pitch and z-axis translation and the combination of X-axis translation, y-axis translation and yaw, which is more difficult to perform with the foot than with the hand.

BACKGROUND OF THE INVENTION

There have been already developed and used various kinds of devices which can be turned on or off with a foot switch and in which the work speed can be controlled with the foot switch. Such foot-switch-operated devices are essential when the user's hands need to be used for other tasks or when a user is not permitted to simultaneously use the feet and the hands for safety purposes.

For example, during the process of a modern surgical operation such as a laparoscopic operation or an ophthalmic operation, a foot switch is additionally operated by a surgeon to cause various kinds devices to perform different functions thereof.

Conventional foot switches are disclosed in U.S. Pat. Nos. 6,132,313 and 5,787,760. The foot switches disclosed in these patents have two rotational degrees of freedom (pitch and yaw) and can make forward and backward movement. However, they are structurally complicated and bulky. In case of the foot switch of the '313 patent, it is necessary to use two different pivot elements because the axes of yaw and pitch are not aligned with each other. An additional space is also required to permit the forward and backward movement. In case of the foot switch of the '760 patent, linear guides have to be used in order to accurately control the movement. Also required is an additional space to permit the forward and backward movement.

A need has existed for a pedal input device capable of easily realizing three degrees of freedom, while enjoying a simplified structure and a reduced volume.

DISCLOSURE OF THE INVENTION

In view of the above-noted problems, it is an object of the present invention to provide a pedal input device with three rotational degrees of freedom in which three-degree-of-freedom movement occurs about a single rotation center, thereby accomplishing a simplified structure and a reduced size.

Another object of the present invention is to provide a pedal input device with three rotational degrees of freedom in which the translational movement of a drive member is caused by rotation of a pedal plate, thereby rendering the device operable with a minimized motion of the user's foot.

In accordance with an embodiment of the present invention, there is provided a pedal input device including: a base plate; a rotation center portion provided at the center of the base plate; a contacting plate rotatably and tiltably fitted to the rotation center portion, the contacting plate having a yaw switch contacting portion protruding downwards from lower surface of the contacting plate, a pedal plate carried by the contacting plate and foot-operated so as to cause a drive member to make three-degree-of-freedom rotational movement (roll, pitch and yaw), three-degree-of-freedom translational movement (x-axis or left-and-right translation, Y-axis or back-and-forth translation and Z-axis or up-and-down translation), the combination of two-degree-of-freedom translation and one-degree-of-freedom rotation (x-axis translation, y-axis translation and yaw), and the combination of two-degree-of-freedom rotation and one-degree-of-freedom translation (roll, pitch and z-axis translation); a pair of pitch switches installed on the base plate in an opposing relationship with each other so that the pitch switches can be alternately S contacted to the contacting plate of the pedal plate; a pair of roll switches installed on the base plate in an perpendicular relationship to the pitch switches so that the roll switches can be alternately contacted to the contacting plate of the pedal plate; and a pair of yaw switches installed on the base plate in an spaced-apart relationship with each other so that the yaw switches can be alternately contacted to the yaw switch contacting portion as the pedal plate rotates.

Preferably, the contacting plate is fixedly secured to the pedal plate so that the pedal plate and the contacting plate can move together.

It is preferred that the rotation center portion includes a ball race provided at the center of the base plate and a ball joint attached to the contacting plate, the ball joint being coupled with the ball race for rotational and pivotal movement relative to the ball race.

Further, the rotation center portion may include a universal joint installed at the center of the base plate for making two-degree-of-freedom rotation (roll and pitch) and a thrust bearing coupled with the universal joint for making one-degree-of-freedom rotation (yaw), the thrust bearing being attached to the contacting plate.

Preferably, the base plate includes a peripheral edge portion, a support rim portion extending along the peripheral edge portion and one or more return spring S portions arranged along the support rim portion in a predetermined interval to resiliently bias the pedal plate into an original position.

Further, the base plate includes a peripheral edge portion and a support rim portion extending along the peripheral edge portion, the contacting plate being connected to the support rim portion by a plurality of radially extending tension springs.

It is preferred that the pitch switches, the roll switches and the yaw switches are electric switches each having a contacting piece.

Preferably, the drive member is a manipulator for actuating a laparoscope used in a laparoscopic operation and a robotic surgery, the manipulator being configured to make three-degree-of-freedom movement including roll, pitch and z-axis translation.

With the present pedal input device with three rotational degrees of freedom, the three-degree-of-freedom movement occurs about a single rotation center, which makes it possible to accomplish a simplified structure and a reduced size. Furthermore, the translational movement of a drive member is caused by rotation of a pedal plate, which makes it possible to minimize the motion of the user's foot.

DETAILED DESCRIPTION OF THE PREFERRED EMBODIMENTS

Hereinafter, one preferred embodiment of the present invention will be described with reference to the accompanying drawings. The following description is made for illustrative purposes to enable a person skilled in the art to carry out the invention with ease but is not intended to limit the scope of the invention.

Figure 1:
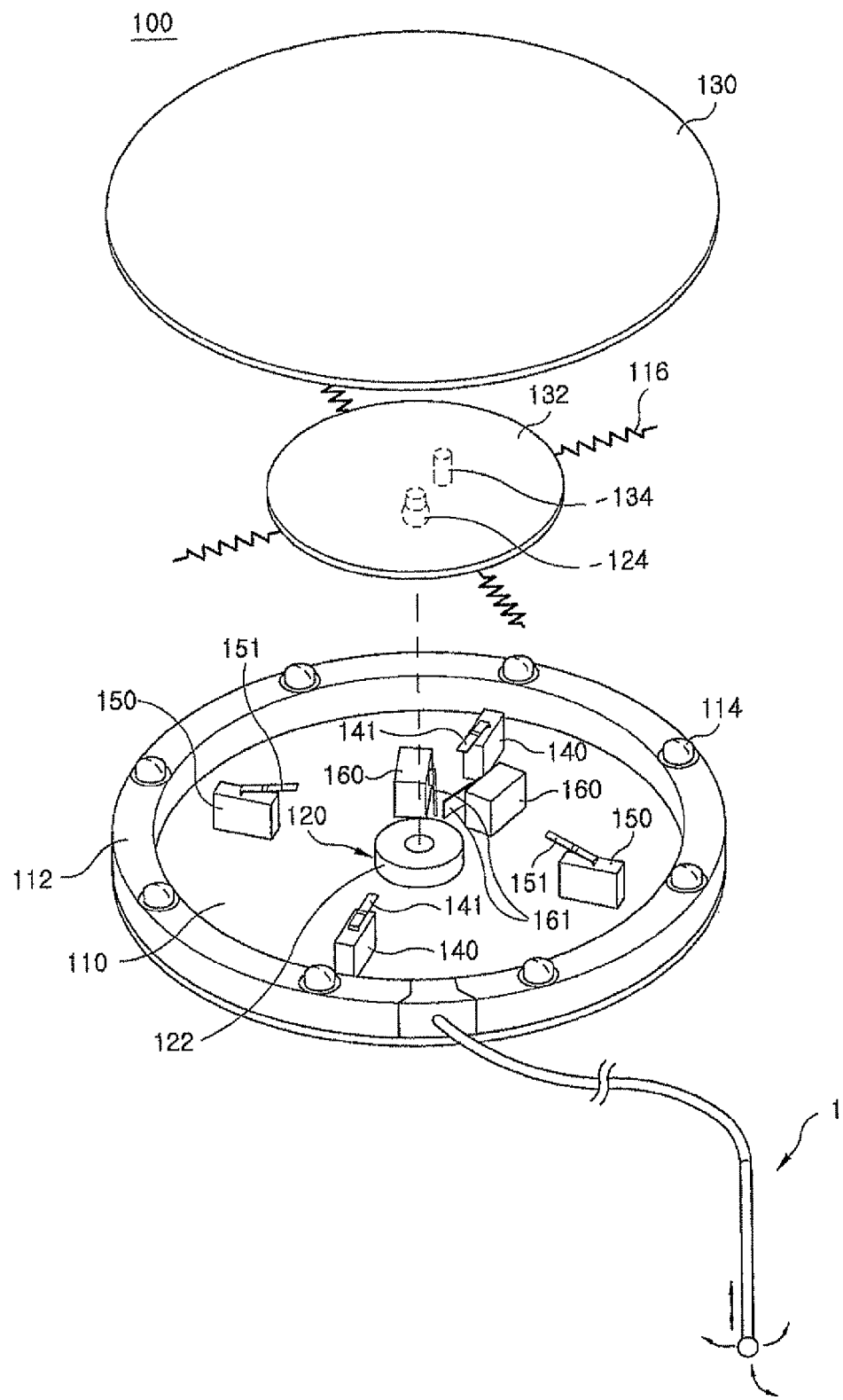
FIG. 1 is an exploded perspective view showing a pedal input device in accordance with one embodiment of the present invention.
Figure 2:
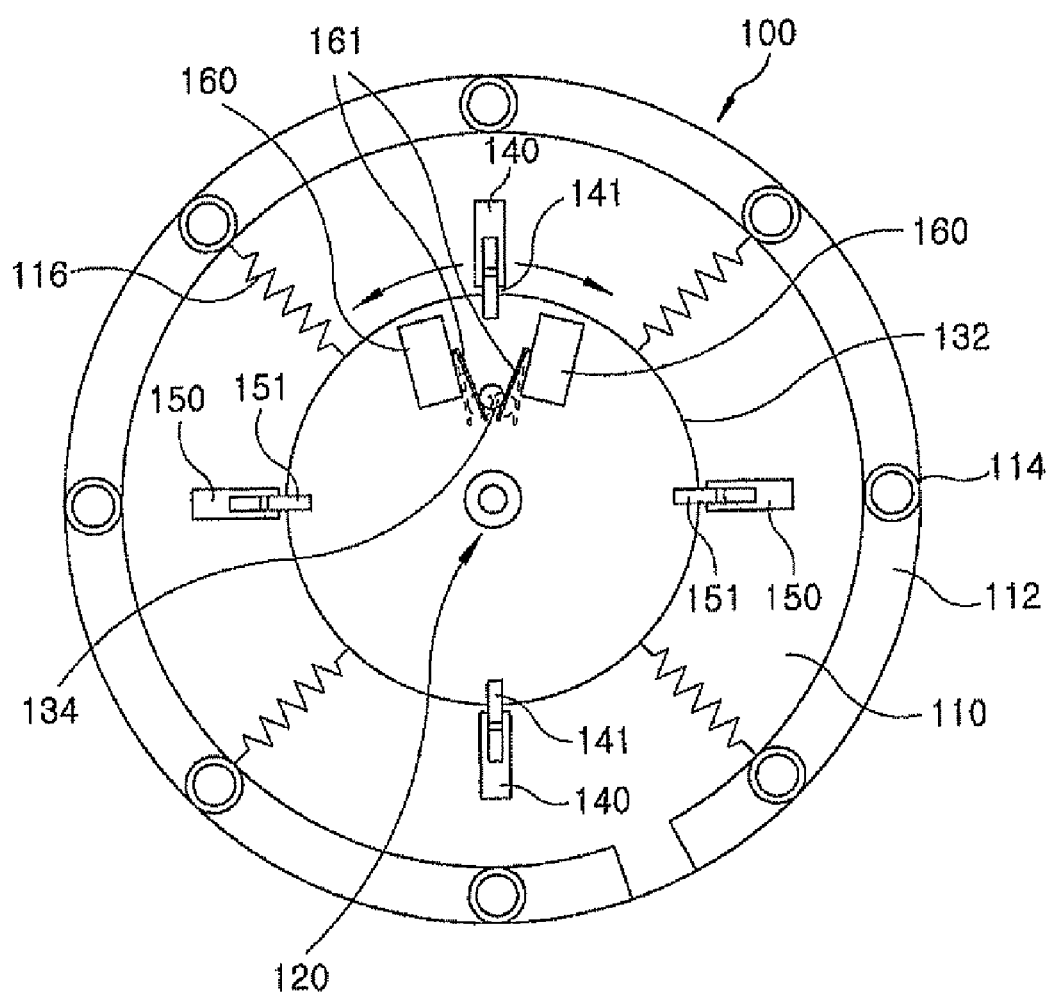
FIG. 2 is a plan view for explaining the yaw movement performed by the pedal input device in accordance with one embodiment of the present invention.
Figure 3:
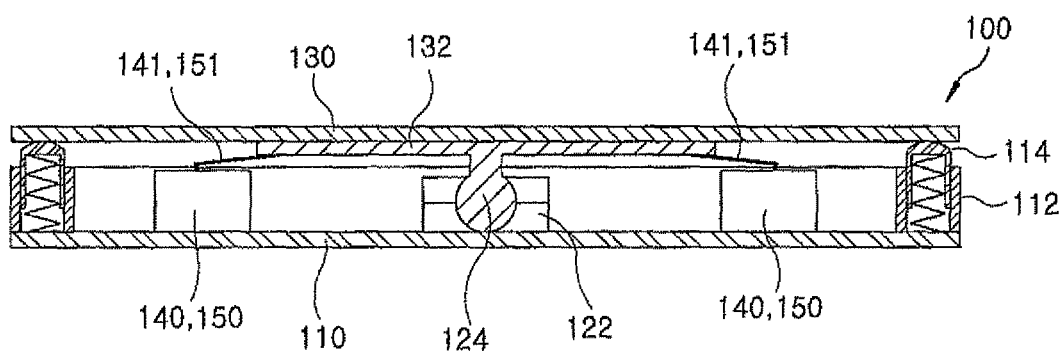
FIGS. 3 and 4 are cross sectional views for explaining the pitch and roll movement performed by the pedal input device in accordance with one embodiment of the present invention.
Figure 4:
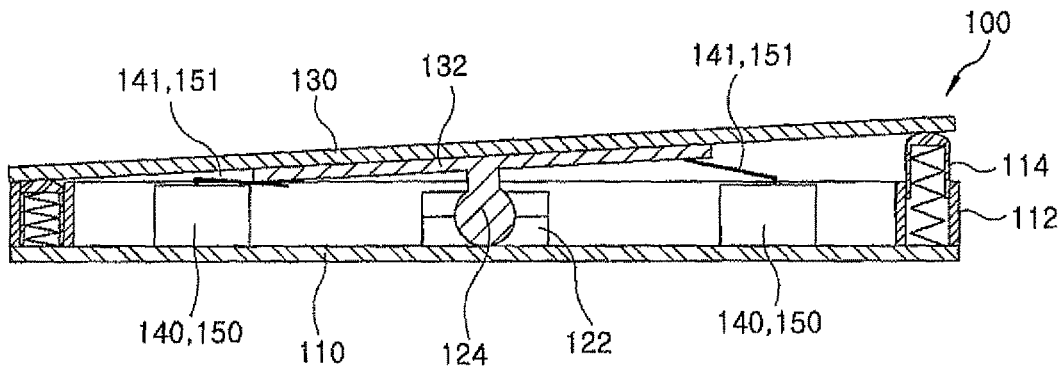

FIG. 1 is an exploded perspective view showing a pedal input device in accordance with one embodiment of the present invention. FIG. 2 is a plan view for explaining the yaw movement performed by the pedal input device in accordance with one embodiment of the present invention. FIGS. 3 and 4 are cross sectional views for explaining the pitch and roll movement performed by the pedal input device in accordance with one embodiment of the present invention.

As shown in FIG. 1, the pedal input device 100 with three rotational degrees of freedom includes a base plate 110, a rotation center portion 120 about which the roll, pitch and yaw movement is made, pitch, roll and yaw switches 140, 150 and 160 arranged on the base plate 110 for generating electric signals needed to operate a drive member 1, and a pedal plate 130 rotatably and tiltably fitted to the rotation center portion 120 and foot-operated to selectively contact the pitch, roll and yaw switches 140, 150 and 160.

The base plate 110 has a circular or polygonal shape and is provided with a flat bottom surface so that it can be placed on the floor. The base plate 110 is made of a metal or a synthetic resin. A rubber member may be attached to the bottom surface of the base plate 110 to enhance the frictional contact of the bottom surface with the floor.

The rotation center portion 120 is installed in the central area of the base plate 110. The rotation center portion 120 ensures that the roll, pitch and yaw movement of the pedal plate 130 is made on one center point. The rotation center portion 120 includes a ball race 122 having a concave groove at its center and a ball joint 124 having a ball portion coupled with the concave groove of the ball race 122. The ball portion makes rolling contact with the concave groove for pivotal and rotational movement.

As an alternative example not shown in the drawings, the rotation center portion 120 may include a universal joint installed at the center of the base plate 110 for making two-degree-of-freedom rotation (roll and pitch) and a thrust bearing coupled with the universal joint for making one-degree-of-freedom rotation (yaw).

A disk-shaped contacting plate 132 is attached to the upper end of the ball joint 124 which is rotatably and tiltably fitted to the rotation center portion 120. The pedal plate 130 is brought into close contact with the upper surface of the contacting plate 132 so that the pedal plate 130 and the contacting plate 132 can move together about the rotation center portion 120.

The contacting plate 132 has a diameter suitable for allowing the contacting plate 132 to make contact with the pitch switches 140, the roll switches 150 and the yaw switches 160. The pedal plate 130 is touched and operated by the user's foot and may have the same area and contour as that of the base plate 110.

The pedal plate 130 and the contacting plate 132 may be fixed together by screws or other fastening means. Arrows or other indicia for indicating the pitch, roll and yaw movement may be provided on the upper surface of the pedal plate 130.

The pitch switches 140 are arranged on the base plate 110 substantially at twelve o'clock and six o'clock positions in FIGS. 1 and 2 in a diametrically opposing relationship with each other. The pitch switches 140 include elastic contacting pieces 141 extending radially inwards. The contacting pieces 141 are electrically connected to the pitch switches 140 so that they can be contacted to the contacting plate 132 in an alternating manner.

The pitch switches 140 are electric units that cause the drive member 1 to make back-and-forth translational movement or pitch movement while the drive member 1 is kept stationary or moving. Although the drive member 1 taken as an example in the illustrated embodiment is a laparoscope manipulator, the present invention may apply to other mechanisms if they can make three-degree-of-freedom rotation (roll, pitch and yaw), three-degree-of-freedom translation (x-axis or left-and-right translation, Y-axis or back-and-forth translation and Z-axis or up-and-down translation), the combination of two-degree-of-freedom translation and one-degree-of-freedom rotation (x-axis translation, y-axis translation and yaw) and the combination of two-degree-of-freedom rotation and one-degree-of-freedom translation (roll, pitch and z-axis translation). Although not shown in the drawings, it may be possible to employ a control unit for controlling electric signals for roll, pitch and yaw movement and a drive unit such as a cylinder or the like.

The roll switches 150 are arranged on the base plate 110 substantially at three o'clock and nine o'clock positions in FIGS. 1 and 2 in a perpendicular relationship to the pitch switches 140. The roll switches 150 include elastic contacting pieces 151 extending radially inwards. The contacting pieces 151 are electrically connected to the roll switches 150 50 that they can be contacted to the contacting plate 132 in an alternating manner.

The roll switches 150 are electric units that cause the drive member 1 to make left-and-right translational movement or roll movement while the drive member 1 is kept stationary or moving.

The yaw switches 160 are arranged on the base plate 110 substantially at one o'clock and eleven o'clock positions in FIGS. 1 and 2 in an adjoining relationship with the pitch switch 140 arranged at the twelve o'clock position.

The yaw switches 160 include contacting pieces 161 provided on the opposing side surfaces thereof. The contacting plate 132 includes a yaw switch contacting portion 134 extending downwards from the lower surface of the contacting plate 132. The yaw switch contacting portion 134 is interposed between the contacting pieces 161 of the yaw switches 160 so that the contacting pieces 161 can make contact with the yaw switch contacting portion 134 in an alternating manner.

In other words, if the contacting plate 132 makes yaw movement out of a horizontal posture, the yaw switch contacting portion 134 is alternately contacted to one of the yaw switches 160, thus causing the drive member 1 to make up-and-down translational movement or yaw movement.

The base plate 110 includes an annular support rim portion 112 extending along the peripheral edge portion thereof and protruding upwards at a specified height. One or more return spring portions 114 are arranged along the support rim portion 112. Preferably, the return spring portions 114 are arranged in an interval of about 45 degrees. Each of the return spring portions 114 is inserted in respective hole in the annular support rim portion 112 and includes a compression spring and a cap mounted thereon. The return spring portions 114 acts to return the pedal plate 130 to an original position at the end of pitch and roll movement.

Tension springs 116 are radially retained between the contacting plate 132 and the support rim portion 112 in order to return the pedal plate 130 and the contacting plate 132 to an original position at the end of yaw movement, i.e., horizontal rotation. The tension springs 116 are circumferentially spaced apart from one another in an interval of about 90 degrees. In addition, the support rim portion 112 may have a cutout for engagement with a connector of the drive member 1.

The pedal input device with three rotational degrees of freedom operates as follows.

Referring to FIGS. 2 through 4, during the course of, e.g., a laparoscopic operation or a robotic surgery, a doctor operates a laparoscope with the pedal input device 100 while holding operation instruments with the hands.

As shown in FIG. 3, the pedal plate 130 is kept horizontal by the return spring portions 114 when the user's foot is not placed on the pedal plate 130. At this time, the contacting plate 132 remains in contact with the contacting pieces 141 and 151 of the pitch switches 140 and the roll switches 150, in which each switch is turned off.

When there is a need to operate the drive member 1, e.g., a laparoscope manipulator, capable of making three-degree-of-freedom movement, namely the combination of roll, pitch and z-axis translation, the user operates the drive member 1 by placing his or her foot on the pedal plate 130.

In order to cause the drive member 1 to make linear up-and-down translational movement, the user rotates the pedal plate 130 to left or right about the rotation center portion 120 in a horizontal posture. As the pedal plate 130 rotates, the yaw switch contacting portion 134 of the contacting plate 132 presses the contacting piece 161 of one of the yaw switches 160, thereby turning on the corresponding one of the yaw switches 160. Thereafter, the pedal plate 130 is returned back to an original position under the biasing force of the tension spring 116 retained between the contacting plate 132 and the support rim portion 112.

If it is necessary to cause the drive member 1 to make pitch movement during its translational movement or stoppage, the pedal plate 130 is tilted forwards or backwards about the rotation center portion 120. In response, the contacting plate 132 presses the contacting piece 141 of one of the pitch switches 140, thereby turning on the corresponding one of the pitch switches 140. At this time, the return spring portions 114 near the pressed pitch switch 140 are compressed and then released to keep the pedal plate 130 horizontal.

Similarly, if it is necessary to cause the drive member 1 to make roll movement during its translational movement or stoppage, the pedal plate 130 is tilted to left or right about the rotation center portion 120. In response, the contacting plate 132 presses the contacting piece 151 of one of the roll switches 150, thereby turning on the corresponding one of the roll switches 150. At this time, the return spring portions 114 near the pressed roll switch 150 are compressed and then released to keep the pedal plate 130 horizontal.

The translation, pitch and roll movement of the drive member 1 is repeatedly and continuously made as the pedal plate 130 is operated by the user in the above-noted manner.

Although the combination of two-degree-of-freedom rotational movement and one-degree-of-freedom translational movement (roll, pitch and z-axis translation) has been described above, the present invention is not limited thereto. By operating the pedal plate 130 about the rotation center portion 120 with three rotational degrees of freedom, it is possible for the drive member 1 to perform three-degree-of-freedom rotational movement (roll, pitch and yaw), three-degree-of-freedom translational movement (x-axis or left-and-right translation, Y-axis or back-and-forth translation and Z-axis or up-and-down translation), and the combination of two-degree-of-freedom translation and one-degree-of-freedom rotation (x-axis translation, y-axis translation and yaw).

With the present pedal input device described above, the three-degree-of-freedom rotation movement occurs about a single rotation center, which makes it possible to accomplish a simplified structure and a reduced size. Furthermore, the translational movement of a drive member is caused by rotation of a pedal plate, which makes it possible to minimize the motion of the user's foot.

While one preferred embodiment of the present invention has been described hereinabove, the present invention is not limited thereto. It will be apparent to those skilled in the art that many different changes and modifications may be made without departing from the scope of the invention defined in the claims.

What is claimed is:

1. A pedal input device comprising:
    a base plate;
    a rotation center portion provided at the center of the base plate;
    a contacting plate rotatably and tiltably fitted to the rotation center portion, the contacting plate having a yaw switch contacting portion protruding downwards from a lower surface of the contacting plate;
    a pedal plate carried by the contacting plate and foot-operated so as to cause a drive member to make three-degree-of-freedom rotational movement, three-degree-of-freedom translational movement, the combination of two-degree-of-freedom translation and one-degree-of-freedom rotation, and the combination of two-degree-of-freedom rotation and one-degree-of-freedom translation;
    a pair of pitch switches installed on the base plate in an opposing relationship with each other so that the pitch switches can be alternately contacted to the contacting plate of the pedal plate;
    a pair of roll switches installed on the base plate in a perpendicular relationship to the pitch switches so that the roll switches can be alternately contacted to the contacting plate of the pedal plate; and
    a pair of yaw switches installed on the base plate in a spaced-apart relationship with each other so that the yaw switches can be alternately contacted to the yaw switch contacting portion as the pedal plate rotates,
    wherein the rotation center portion includes a ball race provided at the center of the base plate and a ball joint attached to the contacting plate, the ball joint being coupled with the ball race for rotational and pivotal movement relative to the ball race.

2. The pedal input device of claim 1, wherein the contacting plate is fixedly secured to the pedal plate so that the pedal plate and the contacting plate can move together.

3. The pedal input device of claim 1, wherein the base plate includes a peripheral edge portion, a support rim portion extending along the peripheral edge portion and one or more return spring portions arranged along the support rim portion in a predetermined interval to resiliently bias the pedal plate into an original position.

4. The pedal input device of claim 1, wherein the base plate includes a peripheral edge portion and a support rim portion extending along the peripheral edge portion, the contacting plate being connected to the support rim portion by a plurality of radially extending tension springs.

5. The pedal input device of claim 1, wherein the pitch switches, the roll switches and the yaw switches are electric switches each having a contacting piece.

6. The pedal input device of claim 1, wherein the drive member is a manipulator for actuating a laparoscope used in a laparoscopic operation and a robotic surgery, the manipulator being configured to make three-degree-of-freedom movement including roll, pitch and z-axis translation.

7. The pedal input device of claim 1, wherein the contacting plate has a disc-shape.

8. The pedal input device of claim 7, wherein the contacting plate has a diameter for allowing the contacting plate to make contact with the pitch switches, the roll switches and the yaw switches.

9. A pedal input device comprising:
a base plate;
a rotation center portion provided at the center of the base plate;
a contacting plate rotatable and tiltably fitted to the rotation center portion, the contacting plate having a yaw switch contacting portion protruding downwards from a lower surface of the contacting plate;
a pedal plate carried by the contacting plate and foot-operated so as to cause a drive member to make three-degree-of-freedom rotational movement, three-degree-of-freedom translational movement, the combination of two-degree-of-freedom translation and one-degree-of-freedom rotation, and the combination of two-degree-of-freedom rotation and one-degree-of-freedom translation;
a pair of pitch switches installed on the base plate in an opposing relationship with each other so that the pitch switches can be alternately contacted to the contacting plate of the pedal plate;
a pair of roll switches installed on the base plate in a perpendicular relationship to the pitch switches so that the roll switches can be alternately contacted to the contacting plate of the pedal plate; and
a pair of yaw switches installed on the base plate in a spaced-apart relationship with each other so that the yaw switches can be alternately contacted to the yaw switch contacting portion as the pedal plate rotates,
wherein the rotation center portion includes a universal joint installed at the center of the base plate for making two-degree-of-freedom rotation and a thrust bearing coupled with the universal joint for making one-degree-of-freedom rotation, the thrust bearing being attached to the contacting plate.

10. The pedal input device of claim 9, wherein the contacting plate is fixedly secured to the pedal plate so that the pedal plate and the contacting plate can move together.

11. The pedal input device of claim 9, wherein the base plate includes a peripheral edge portion, a support rim portion extending along the peripheral edge portion and one or more return spring portions arranged along the support rim portion in a predetermined interval to resiliently bias the pedal plate into an original position.

12. The pedal input device of claim 9, wherein the base plate includes a peripheral edge portion and a support rim portion extending along the peripheral edge portion, the contacting plate being connected to the support rim portion by a plurality of radially extending tension springs.

13. The pedal input device of claim 9, wherein the pitch switches, the roll switches and the yaw switches are electric switches each having a contacting piece.

14. The pedal input device of claim 9, wherein the drive member is a manipulator for actuating a laparoscope used in a laparoscopic operation and a robotic surgery, the manipulator being configured to make three-degree-of-freedom movement including roll, pitch and z-axis translation.

15. The pedal input device of claim 9, wherein the contacting plate has a disc-shape.

16. The pedal input device of claim 15, wherein the contacting plate has a diameter for allowing the contacting plate to make contact with the pitch switches, the roll switches and the yaw switches.

* * * * *